United States Patent
Vella

(10) Patent No.: US 11,297,848 B2
(45) Date of Patent: Apr. 12, 2022

(54) COMPOSITIONS OF WHOLE GREEN COFFEE BEAN PRODUCTS AND WHOLE HEMP PRODUCTS

(71) Applicant: GOBEAN GREEN COFFEE PRODUCTS, LLC

(72) Inventor: Thomas Vella, Scottsdale, AZ (US)

( * ) Notice: Subject to any disclaimer, the term of this patent is extended or adjusted under 35 U.S.C. 154(b) by 155 days.

(21) Appl. No.: 16/388,869

(22) Filed: Apr. 19, 2019

(65) Prior Publication Data

US 2019/0239529 A1 Aug. 8, 2019

Related U.S. Application Data

(63) Continuation-in-part of application No. 16/149,412, filed on Oct. 2, 2018, now Pat. No. 11,083,769, which is a continuation-in-part of application No. 14/716,869, filed on May 19, 2015, now Pat. No. 10,086,031, which is a continuation-in-part of application No. 13/215,174, filed on Aug. 22, 2011, now Pat. No. 9,034,410.

(51) Int. Cl.
| | |
|---|---|
| *A23F 5/02* | (2006.01) |
| *A23F 5/08* | (2006.01) |
| *A23P 10/40* | (2016.01) |
| *A23P 10/30* | (2016.01) |
| *A23L 3/28* | (2006.01) |
| *A23L 3/3418* | (2006.01) |
| *A23L 29/00* | (2016.01) |
| *A61K 36/185* | (2006.01) |

(52) U.S. Cl.
CPC .................. *A23F 5/02* (2013.01); *A23F 5/08* (2013.01); *A23L 3/28* (2013.01); *A23L 3/3418* (2013.01); *A23L 29/015* (2016.08); *A23P 10/30* (2016.08); *A23P 10/40* (2016.08); *A61K 36/185* (2013.01); *A23V 2002/00* (2013.01); *A23V 2250/1578* (2013.01); *A23V 2250/161* (2013.01); *A23V 2250/1618* (2013.01); *A23V 2250/1628* (2013.01); *A23V 2250/2132* (2013.01); *A23V 2300/14* (2013.01); *A23V 2300/31* (2013.01); *A61K 2236/13* (2013.01); *A61K 2236/15* (2013.01); *A61K 2236/17* (2013.01)

(58) Field of Classification Search
None
See application file for complete search history.

(56) References Cited

U.S. PATENT DOCUMENTS

| | | | |
|---|---|---|---|
| 9,034,410 B2 * | 5/2015 | Vella | A61K 36/74 426/595 |
| 10,086,031 B2 * | 10/2018 | Vella | A23F 5/08 |
| 2018/0125088 A1 * | 5/2018 | Jamroz | A23F 5/14 |

* cited by examiner

*Primary Examiner* — Susan Hoffman
(74) *Attorney, Agent, or Firm* — Allen F. Bennett; Bennett Intellectual Property

(57) ABSTRACT

Disclosed are novel processing methods for green coffee beans that result in novel green coffee bean products, including products that incorporate whole green coffee beans which is combined with a whole hemp powder or CBD. Methods for processing green coffee beans include selecting whole coffee beans in their fresh green unroasted state with naturally-occurring levels of phytonutrients, sterilizing and drying them, applying iterative grinding processes and stabilization techniques, all while avoiding high temperatures. A similar method is used to prepare a whole hemp powder, which may then be combined with the whole green coffee bean powder.

12 Claims, 3 Drawing Sheets

COMPOSITIONS OF WHOLE GREEN COFFEE BEAN PRODUCTS AND WHOLE HEMP PRODUCTS

CROSS-REFERENCE TO RELATED APPLICATIONS

This application is a Continuation-in-Part of U.S. patent application Ser. No. 16/149,412 filed on Oct. 2, 2018, now U.S. Pat. No. 11,083,769, which is a Continuation-in-Part of U.S. patent application Ser. No. 14/716,869 filed on May 19, 2015, which issued as U.S. Pat. No. 10,086,031 on Oct. 2, 2018, which is a Continuation-in-Part of U.S. patent application Ser. No. 13/215,174 filed on Aug. 22, 2011, which issued as U.S. Pat. No. 9,034,410 on May 19, 2015.

BACKGROUND OF THE INVENTION

Field of the Invention

The present invention relates to compositions of whole green coffee beans powders and whole hemp powders, and methods of processing coffee beans and hemp to manufacture the powders combined to create the compositions.

Description of the Related Art

Coffee Bean Products

Worldwide, caffeine is the most widely consumed substance having psychoactive effects. It is the neuroactive agent in coffee and tea, and it is a nonselective antagonist of the neuromodulator adenosine; if applied in commonly consumed doses, it generates stimulating effects by blockading adenosine receptors. Cognitive performance generally is positively influenced by caffeine ingestion, and the influence of caffeine on cognitive performance is well documented. Although some studies show limited benefit to performance, caffeinated coffee is the most common form of caffeine intake, increasing alertness and lowering fatigue. Caffeine is now readily available in a variety of liquid (i.e., energy drinks) and capsule forms.

The term "coffee bean" collectively refers to the seeds (coffee seeds) that are obtained by the refining process of removing the pulp and the skin from the berries (known as coffee berries or coffee cherries) of Coffea plants, and the beans that are produced from these. Coffee berries, which contain the coffee bean, are produced by several species of small evergreen plants of the genus *Coffea*, which are of the family Rubiaceae. The two most commonly grown species are *Coffea robusta* (also known as Coffea canephora) and *Coffea arabica*. These are typically cultivated in Latin America, Southeast Asia, and Africa. "Green" coffee beans are coffee beans that have not yet passed through a roasting process, such as the roasting process used in the production of coffee.

The various steps in the production of coffee are described in Smith, A. W., in Coffee; Volume 1: Chemistry pp 1-41, Clark, R. J. and Macrea, R. eds, Elsevier Applied Science London and New York, 1985; Clarke, R. J., in Coffee: Botany, Biochemistry, and Production of Beans and Beverage, pp 230-250 and pp 375-393; and Clifford, M. N. and Willson, K. C. eds, Croom Helm Ltd, London, as described in U.S. patent application Ser. No. 12/941,557 titled Modulation Of Coffee Flavour Precursor Levels In Green Coffee Grains, filed Nov. 8, 2010 on behalf of McCarthy, et al., and published on May 26, 2011 as publication number U.S. 2011/0126314 A1 (hereafter "McCarthy"), the entirety of which is incorporated herein by reference as though set forth in full herein. The process typically starts with the collection of mature, ripe red coffee cherries. The outer layer, or pericarp, can then be removed using either the dry or wet process. The dry process is the simplest and involves: (1) classification and washing of the cherries; (2) drying the cherries after grading (either air drying or mechanical drying); and (3) dehusking the dried cherries to remove the dried pericarp. The wet process is slightly more complicated, and generally leads to the production of higher quality green beans. The wet process is more often associated with C. arabica cherries. The wet process may comprise: (A) classification of the cherries; (B) pulping of the cherries (this step is done soon after harvest and generally involves mechanical removal of the "pulp", or pericarp, of the mature cherries); (C) "fermentation," where the mucilage that remains attached to the grain of the cherries after pulping is removed by allowing the grain plus attached mucilage to be incubated with water in tanks using a batch process. The "fermentation" process is allowed to continue up to 80 hours, although often 24 hours is generally enough to allow an acceptable fermentation and to cause the pH to drop from around 6.8-6.9 to 4.2-4.6, due to various enzymatic activities and the metabolic action of microorganisms which grow during the fermentation. The next steps, (D) drying, involves either air or mechanical hot air drying of the fermented coffee grain, and (E) "hulling," involves the mechanical removal of the "parch" of the dried coffee grain (dried parchment coffee) and often the silverskin. After wet or dry processing, the resulting green coffee grain are often sorted, with most sorting procedures being based on grain size and/or shape.

The next step in the production of conventional coffee is the roasting of the green grain after dehusking or dehulling of dry or wet processed coffee, respectively. This is a time-dependent process which induces significant chemical changes in the bean. The first phase of roasting occurs when the supplied heat drives out the remaining water in the grain. When the bulk of the water is gone, roasting proper starts as the temperature rises towards 374-392 degrees Fahrenheit. The degree of roasting, which is usually monitored by the color development of the beans, plays a major role in determining the flavor characteristics of the final beverage product. Thus, the time and temperature of the roasting are tightly controlled in order to achieve the desired coffee flavor profile. After roasting, the coffee is ground to facilitate extraction during the production of the coffee beverage or coffee extracts (the latter to be used to produce instant coffee products). Again, the type of grinding can influence the final characteristics of the product, such as the flavor of the beverage.

While a considerable amount of research has been carried out on the identification of the flavor molecules in coffee, much less work has been done regarding the physical and chemical reactions that occur within the coffee grains during each of the processing steps. This latter point is particularly evident for the roasting reaction, where the large number of grain constituents undergo an extremely complex series of heat induced reactions (Homma, S. 2001, In "Coffee: Recent Developments". R. J. Clarke and O. G. Vitzthum eds, Blackwell Science, London; Yeretzian, C., et al ((2002) Eur. Food Res. Technol. 214, 92-104; Flament, I (2002) Coffee Flavor Chemistry, John Wiley and Sons, UK; Reineccius, G. A., "The Maillard Reaction and Coffee Flavor" Conference Proceedings of ASIC, 16th Colloque, Kyoto, Japan 1995).

While the details of most of the reactions that occur during the different steps of coffee processing remain relatively unclear, it is understood that the conventional roasting process likely destroys or degrades many beneficial components present in green coffee beans, including phytonutrients such as, for example, Chlorogenic acid. Chlorogenic acids (CGA) are a family of esters formed between certain hydroxycinnamic acids (i.e. caffeic and feluric acids) and (−)-quinic acid. Green (or raw) coffee is a major source of CGA in nature (5-12 g/100 g) (Farah et al. Braz J Plant Physiol. 365 2006; 18:23-36). The major CGA in green coffee are 3-, 4- and 5-caffeoylquinic acids (3-, 4- and 5-CQA), 3,4-, 3,5- and 4,5-dicaffeoylquinic acids (3,4-, 3,5-, and 4,5-diCQA); 3-, 4- and 5-feruloylquinic acids (3-, 4- and 5-FQA) and 3-, 4- and 5-p-coumaroylqunic acids (3-, 4-, and 5-p-CoQA). Caffeoylferuloylquinic acids (CFQA) are minor CGA compounds also found in green coffee, especially in *Coffea robusta* species, as described in U.S. patent application Ser. No. 263,292 titled Effects Of A Decaffeinated Green Coffee Extract On Body Weight Control By Regulation Of Glucose Metabolism, filed Oct. 31, 2008 on behalf of Lemaire, et al., and published on May 6, 2010 as publication number U.S. 2010/0112098 A1 (hereafter "Lemaire"), the entirety of which is incorporated herein by reference as though set forth in full herein. Very small amounts of CGA lactones formed by heating during primary processing may also be observed (Farah et al. Braz J Plant Physiol. 2006, 18:23-36. —Farah et al. J Agric Food Chem. 2005; 53:1505-13).

While green coffee beans have recently been recognized to have some potentially important health benefits (see, e.g., Lemaire, above), products created from green coffee beans have not been widely available like roasted coffee. Part of the reason for this is that processing, preserving and packaging coffee beans in their nutritious, unroasted, "green" state has been difficult, expensive and generally not feasible. For example, Lemaire teaches only extracting certain substances from the green coffee bean, not processing of the entire green coffee bean.

Accordingly, what is needed is an improved method of processing green coffee beans, including partial or whole green coffee beans, that can be used to more easily and inexpensively create green coffee bean products, such as capsules, tablets, mixes, additives, supplements, and the like. Such an improved method is needed to unlock the potential health benefits to consumers of relatively inexpensive products created with green coffee beans, especially whole green coffee beans.

Hemp Products

Numerous benefits have recently been shown to be provided by various compounds found in hemp plants. THC and CBD (cannabidiol) are currently the most well-known beneficial components of the hemp plant. However many other compounds as shown in FIG. 1 are also desirable.

Current methods for extracting various isolates from the hemp plant typically isolate and purify a single chemical from the plant. However, highly concentrated forms of a single compound can lead to ingestion of dosages far higher than required. Overuse of these compounds can lead to undesirable results. Purification of one or a handful of individual chemicals also removes many other ingredients that are beneficial and work synergistically with the isolates. Furthermore, these extraction and purification methods can be costly and time intensive.

The above-described deficiencies of today's systems are merely intended to provide an overview of some of the problems of conventional systems, and are not intended to be exhaustive. Other problems with the state of the art and corresponding benefits of some of the various non-limiting embodiments may become further apparent upon review of the following detailed description.

In view of the foregoing, it is desirable to provide a composition combining both whole green coffee bean products and whole hemp products that include the beneficial aspects of both plants.

BRIEF SUMMARY OF THE INVENTION

Disclosed are novel processing methods for green coffee beans that result in novel green coffee bean products, including products that incorporate whole green coffee beans. More specifically, provided in certain embodiments is a method of processing whole green coffee beans to create stabilized whole green coffee bean mixtures, that includes the steps of: selecting whole coffee beans in their fresh green unroasted state with naturally-occurring levels of phytonutrients; sterilizing the coffee beans; reducing the moisture content of the coffee beans; grinding the coffee beans; and mixing at least one stabilizer into the ground coffee beans; wherein all of the aforesaid steps are accomplished without exposing the coffee beans to high enough temperatures for a sufficient amount of time to substantially degrade the naturally-occurring levels of phytonutrients in the coffee beans. In certain embodiments, all of the aforesaid steps are accomplished without exposing the coffee beans to temperatures exceeding about 130 degrees Fahrenheit for more than a few seconds. The whole green coffee beans may comprise *Coffea robusta* coffee beans, and the phytonutrients may include Chlorogenic acid, including in some embodiments at least two percent by weight of Chlorogenic acid. The step of reducing the moisture content of the coffee beans may comprise reducing the moisture content of the coffee beans to less than about two percent. The at least one stabilizer may comprises at least one of, or all of, Magnesium Silicate; Silicon Dioxide; Tricalcium Phosphate.

In various embodiments, the step of grinding the coffee beans may comprise a plurality of iteratively finer grinding steps, such as three increasingly fine steps. For example, the step of grinding the coffee beans may result in most of the ground coffee bean material being sized to pass through a 20 mesh screen.

Also provided are novel processing methods for whole hemp products, or alternatively CBD mixtures, which may be combined with the whole green coffee bean products to form a composition of both products. In one embodiment, the process includes drying the whole hemp plants by dehumidifying at a temperature below 100° F. The plant material is then ground to a fine mesh. Finally UV light and/or oh zone is used to sterilize the hemp powder.

These and other objects and advantages of the present invention will become apparent from a reading of the attached specification and appended claims. There has thus been outlined, rather broadly, the more important features of the invention in order that the detailed description thereof that follows may be better understood, and in order that the present contribution to the art may be better appreciated. There are features of the invention that will be described hereinafter and which will form the subject matter of the claims appended hereto.

BRIEF DESCRIPTION OF THE DRAWINGS

Further features, advantages and characteristics of the present invention will become apparent to a person of ordinary skill in the art in view of the following detailed discussion of example embodiments of the present invention, made with reference to the drawings annexed, in which.

DETAILED DESCRIPTION

Figure 1:
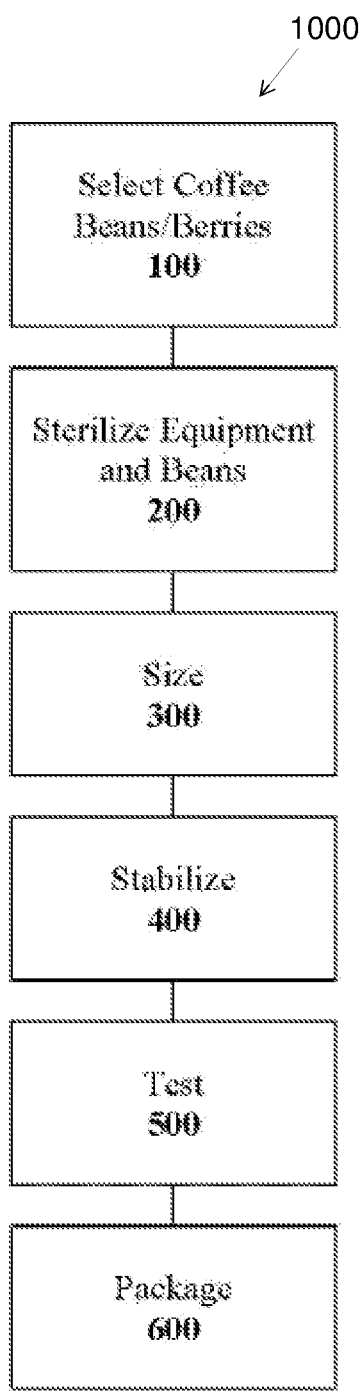
FIG. 1 provides a flow chart showing example steps of a method for processing whole green coffee beans and generating resulting whole green coffee bean products.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Methods for Preparing Whole Green Coffee Bean Products

FIG. 1 shows a process 1000 for preparing whole or partial green coffee beans for tableting, encapsulation, and or other nutritional uses such as mixes, additives, supplements, and the like. Process 1000 has been developed to tend to preserve the Chlorogenic Acid and other phytonutrient content of the green coffee beans by using relatively low temperatures, for instance in one example not more than about 130 degrees Fahrenheit, throughout the processing steps.

Step 1—Berry Selection

The first step in process 1000 is berry selection 100. Whole coffee beans are selected in their fresh green unroasted state, preferably with high levels of Chlorogenic Acid and other naturally occurring phytonutrients. For example, the *Coffea robusta* species of berries may be selected. However, any suitable berry or combination of berries may be selected.

Step 2—Sterilization

Figure 2:
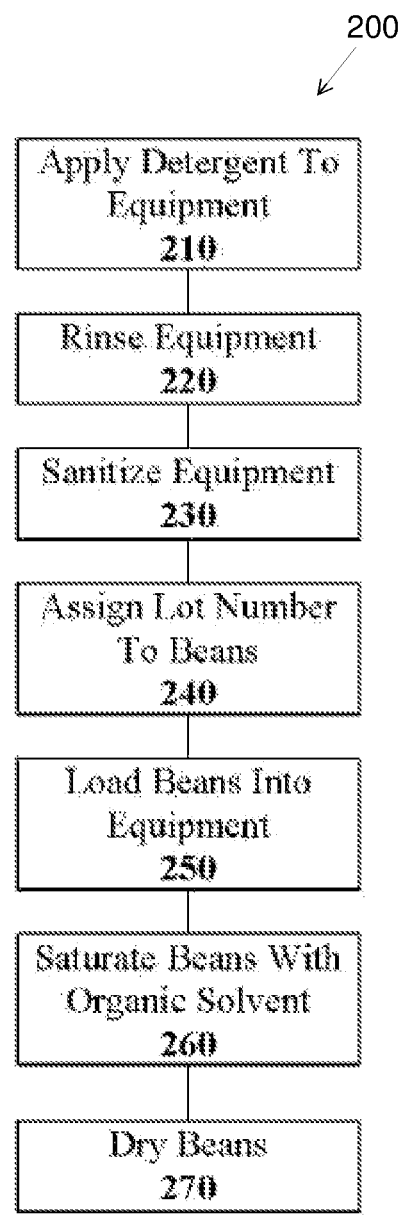
FIG. 2 provides a flow chart showing example sterilization steps of a method for processing whole green coffee beans and generating resulting whole green coffee bean products.

Turning to FIG. 2, in the second step, sterilization 200, the processing machinery must be sterilized. The machinery, such as a ribbon mixer, should be sanitized to make certain that it is clean and free from any debris from products that were processed prior to green coffee. The machinery may also be cleaned with an industrial strength sanitizing solution that kills microbial contamination. In one embodiment, the machinery comprises a Weiler & Company Model 1660 thirty cubic foot ribbon mixer that may be cleaned in a three-step process. In step one, the detergent phase 210, the mixer may be cleaned with trisodium phosphate or similar substance to remove any filth or debris. In step two, clear water rinse 220, the mixer is rinsed thoroughly with clean potable water to remove any detergent residue. Then in step three, the sanitizing phase 230, all food contact surfaces may be saturated with alcohol or other appropriate organic solvent, such as a 70% isopropyl alcohol (IPA) solution, and allowed to air dry.

The whole green coffee beans may have a lot number assigned 240 for the purposes of batch control, for instance in compliance with current Good Manufacturing Practices for Dietary Supplements (cGMP), pursuant to 21 CFR 111. A predetermined amount of the green coffee beans are loaded 250 in the equipment, such as a properly sanitized ribbon mixer. For example, in one embodiment, 100 to 300 kilograms of whole green coffee beans are loaded 250 into a properly sanitized thirty cubic foot ribbon mixer.

The whole green coffee beans are then saturated 260 with an appropriate organic solvent such as IPA. The saturated beans are then dried 270 in a hygienic manner. The saturated beans may be dried by, for instance, removing them from the ribbon mixer and placing them evenly on clean paper-lined trays that are placed in drying racks. The drying Racks may then be moved into a climate controlled drying room set at, for instance, 120-130 degrees Fahrenheit, until they are completely dried. This may take approximately twelve to twenty-four hours, for example to reduce the moisture level of the beans from a typical fifteen percent to less than, for example, two percent.

While example sterilization steps have been provided above, any suitable means of sterilization may be used. A means of sterilization should be suitable if it sufficiently kills yeast, mold, bacteria, and viral contamination that may be present on the beans. This is preferably done for the safety of those consuming the product, and for the purpose of extending the shelf life of the products of which the green coffee beans will become a part. The heating and/or drying aspect 270 of the example process also serves to extend shelf life, as well as to expedite the steps that follow.

Step 3—Sizing

Figure 3:
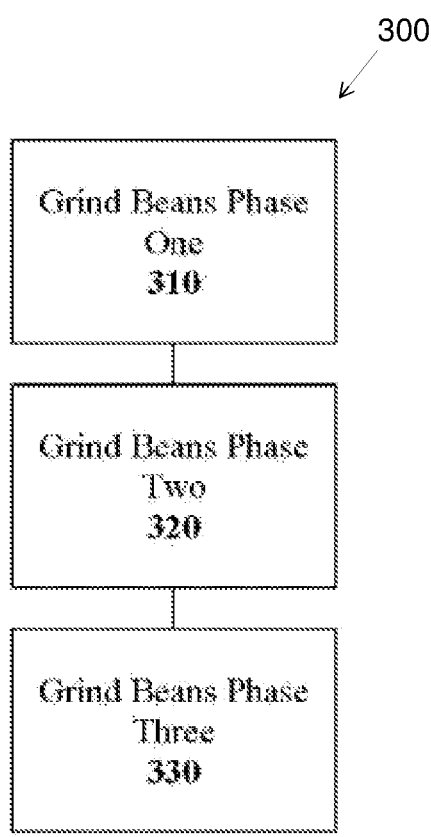
FIG. 3 provides a flow chart showing example sizing steps of a method for processing whole green coffee beans and generating resulting whole green coffee bean products.

The third step, sizing 300, an iterative example of which is illustrated in FIG. 3, may be performed using a coffee-grinding mill. Typical coffee-grinding mills tend to generate a great deal of friction and heat. In order to keep the temperature of the beans relatively low during this process, for instance under about 130 degrees Fahrenheit, the whole green coffee beans may be ground down to successively smaller sizes in a plurality of iterative phases. For example, one embodiment employs three iterative phases. In Phase One 310, the sterilized and dried beans are passed through a grinder, such as a Modern Process Equipment 3 HP Coffee Grinder, reducing the size of the bean to, for instance, a minus 8-10 mesh screen size. Then in Phase Two 320, the grinder setting is reduced, for instance from course setting 1 to 3, and the Phase One material is passed through the grinder, further reducing the size so that the material will pass through, for instance, a 12-16 mesh screen. Next, in Phase Three 330, the grinder setting is reduced again, for instance from a course setting 3 to a medium setting in the range of 3 to 7, and the Phase Two material is passed through the mill again until all of the material passes through a smaller screen, such as, for instance, a 20 mesh screen.

Like the other examples provided herein, the above example sizing step 300 is just illustrative of the concept, and the invention is not limited to any of these specific steps unless otherwise stated in the claims. The point is that grinding or milling green coffee is difficult. To preserve its nutritional integrity during the sizing step 300, the green coffee material should not be forced through the mill in a manner that would generate excessive heat, for instance heat that would raise the temperature of the green coffee material above about 130 degrees Fahrenheit. For example, instead of filling or stuffing the grinder with green coffee material and letting it grind, green coffee material can be introduced to the grinder at approximately the same rate as the grinder grinds it on a particular setting.

Note that higher temperatures could be used at various steps and still fall within the scope of the invention, however incremental degradation of the green coffee would likely start to occur according to a time-temperature relationship. For example, the green coffee beans/material may be able to be subject to temperatures exceeding 130 degrees Fahrenheit for several seconds without materially degrading its nutritional components.

Step 4—Stabilization

Figure 4:
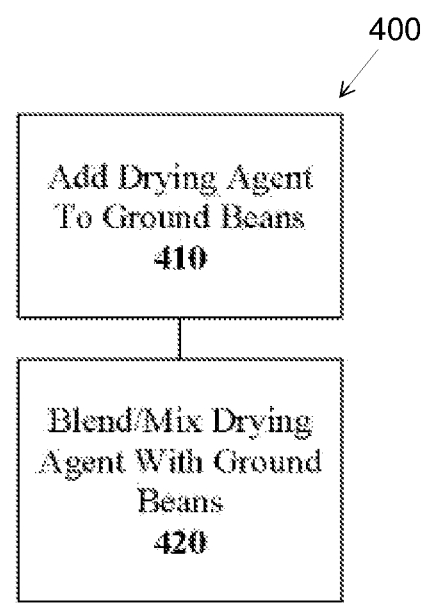
FIG. 4 provides a flow chart showing example steps of a method for stabilizing whole green coffee beans and generating resulting whole green coffee bean products.

Next, the finely ground whole green coffee bean material may be stabilized 400 as illustrated in FIG. 4. During this step 400 the whole green coffee beans that have been ground and classified to predetermined specifications as described above may be placed in a properly sanitized blender. For example, the green coffee bean material may be placed in a Patterson Kelley Twin V sixty-five cubic foot blender that has been sanitized using the three-step process 210, 220, 230 described above. A drying agent may then be introduced 410 to the green coffee bean material. Suitable drying agents may include, for example, Magnesium Silicate, Silicon Dioxide, Tricalcium Phosphate, and the like.

In one example embodiment of the stabilization step 400, six hundred kilograms of sterilized and ground green coffee is placed into a sterilized Patterson Kelley Twin V sixty-five cubic foot blender. Added into the ground green coffee in this example is one to two percent each (by weight) of Magnesium Silicate, Silicon Dioxide, and Tricalcium Phosphate through a 12 mesh screen. That combination may then be blended or mixed 420 for ten minutes at twenty-four revolution per minute, creating an example stabilized whole green coffee bean mixture.

While example stabilization steps 410, 420 are described above, any suitable stabilization procedure may be used. Suitable stabilization procedures are those that assist in the long-term preservation of the whole green coffee bean material, as well as the Chlorogenic acid, essential oils and other phytonutrients naturally present in the green coffee beans. Suitable stabilization procedures also typically provide an anti-caking effect that tends to keep the material from clumping when in storage, and tends to provide a free-flowing powder that facilitates the material being tableted, encapsulated, or otherwise used in nutritional products.

Step 5—Testing

Figure 5:
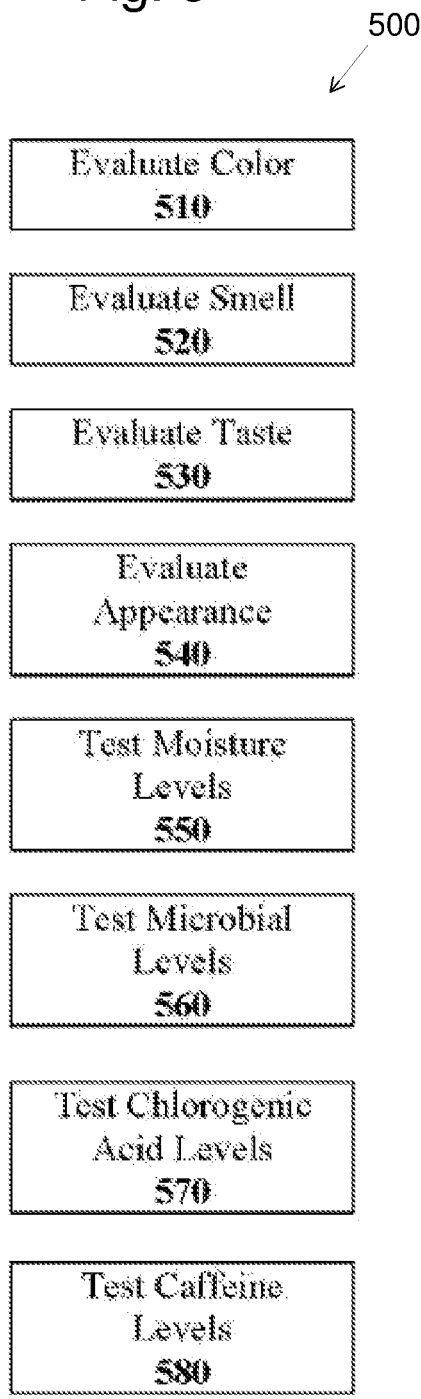
FIG. 5 provides a flow chart showing example steps of a method for testing whole green coffee beans and generating resulting whole green coffee bean products.

Portions of the stabilized whole green coffee bean mixtures may be tested 500, as shown in FIG. 5. Several parameters may be tested or otherwise evaluated in any appropriate order, including, for example, color 510, odor 520, taste 530, appearance 540, moisture levels 550, microbial levels 560, Chlorogenic acid levels 570, caffeine levels 580, and any other suitable testing, for instance as may be required for various nutritional applications.

For example, color testing 510 may be accomplished by matching the color of the material to a light green laboratory control sample. The material passes if it is the typical color of ground green coffee. The material fails if it is not the typical color of ground green coffee. Similarly, odor or smell testing 520 may be accomplished by, for example, matching the smell of the material to a laboratory control sample. The material passes if it has the typical odor of ground green coffee. The material fails if it does not have the typical odor of ground green coffee. Likewise, taste testing 530 may be accomplished by, for example, matching the taste of the material to a laboratory control sample. The material passes if it has the typical taste of ground green coffee. The material fails if it does not have the typical taste of ground green coffee.

Appearance testing 540 may be accomplished by, for example, passing the material through a 20 mesh screen. The material may be considered to pass if 99% or more passes through the screen.

Moisture level testing 550 may be accomplished by, for example, testing the moisture level of the material. The material may be considered to pass if the moisture level is not more than two percent.

Microbial level testing 560 may be accomplished in various way, including, for example, passing the material if it has a total plate count of not more than 1000, yeast and mold test negative, and coliform tests negative.

Chlorogenic acid level testing 570 may be accomplished using known means.

The material may be considered to pass if, for instance, the Chlorogenic acid levels are not less than two percent.

Caffeine level testing 580 may be accomplished using known means. What levels are considered to pass may change in view of the caffeine level desired in the finished product. Unless otherwise specified, the caffeine level should be the same as naturally occurs in green coffee beans.

The above testing regimens are examples only and are not limiting. Any suitable testing may be performed at any stage of the process 1000.

Step 6—Packaging

Figure 6:
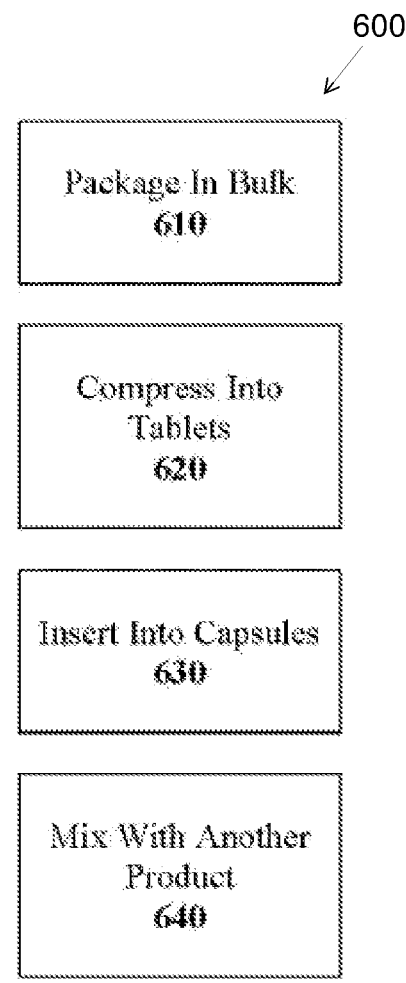
FIG. 6 provides a flow chart showing example steps of a method for packaging whole green coffee beans and generating resulting whole green coffee bean products.

The stabilized whole green coffee bean mixtures described above may be packaged 600 in any of numerous ways, some of which are shown in FIG. 6, and many of which are made possible, or at least especially easier, by the foregoing steps. The stabilized whole green coffee bean mixtures may be packaged as oral dosage forms in typical dietary supplement format, added to foods, and/or delivered in a medium for topical, cosmetic use (such as in a cream or ointment, for example). If the stabilized whole green coffee bean mixture is to be consumed directly (as a food additive, for example), it may be flavored, and thereby serve as a dual-purpose product (as a drink-flavoring agent, for example).

For example and not by way of limitation, in certain embodiments the unique and novel stabilized whole green coffee bean mixtures may be packaged 610 in bulk powder form, may be readily compressed 620 into tablets, may be readily inserted 630 into capsules, or may be mixed 640 with another nutritional supplement or product.

The Methodology and thought process of the invention for whole plant processing is different from convention extraction methodologies, concepts and practices. Typically, science discovers that certain isolates of a plant offer health benefits. For example CBD isolate found in the marijuana plant and hemp plant has health benefits that may help people who have cancer. Typically, the CBD is extracted and purified. However, just like with coffee beans, there are many additional valuable nutrients in the hemp plant that are lost during extraction. FIG. 1 shows the most popular isolates found in the hemp plant all offering health benefits.

Conventional wisdom tells us that extraction of an identified, particularly isolate should be extracted and purified to maximize the benefits. For example, isolate CBD and have humans consume the isolate in its purest form. FIG. 2 shows a typical extraction method for isolating various components of the hemp plant. The thought process behind this is absorption in the body. Isolates are easily absorbed by the body. However, isolates made from the extraction process often cause adverse side effects. For example, caffeine is the world's leading energy drink ingredient for humans. Coffee, energy drinks all contain extracted caffeine typically at a rate of 99% pure. Even in small doses of 80 to 150 mg, a typical dose, can cause jitters, increase heart rate, spike and crash. In some cases cardiac arrest can occur.

Through a patented process of making Whole Green Coffee Powder from Whole unroasted coffee beans, GoBean® was able to eradicate all or most of the negative side effects from caffeine. GoBean® also learned that by consuming all of the whole bean it offered many other health benefits like weight loss, better mood, energy, focus, glucose control and helping with hypertension.

Method for Preparing Whole Hemp Products

Hemp and Marijuana plants are now becoming mainstream and the industry is focused on isolating THC and/or CBD and offering these compounds in their purest form. However, without being bound by theory, the inventor believes that there are many additional health benefits to consuming vitamins, minerals and medicines from the whole verses the isolate made by extraction.

Whole Food Processing (WFP) is a completely different technology than preserves all of the living organisms in the plant. This also delivers the plant's full spectrum, i.e. all of the plant's attributes, not just an isolated one or two. This also means that the body can easily metabolize the nutrients including over 200 terpenes, a group of phytochemicals which are also produced by hemp.

All hemp must be cut from the farm. Once it is cut the plant must be dried before it goes into any kind of processing. Currently some methods include hanging the hemp in barns, some include using drying machines. Once the plant is dry it is shipped to a manufacturing facility to be processed into some kind of isolate.

WFP Hemp Methods

1) Our process also includes the drying process however WFP uses low heat 100 degrees Fahrenheit or less and incorporates dehumidification by means of a dehumidifier. With the help of this process WFP is able to get the plant dried less than 5% moisture content.

2) Once the plant is dried it is ground to a fine mesh. The mesh rate is between 30 and 100 mesh.

3) Once the powder is dried and ground it goes through a non-chemical sterilizing process, for example exposure to UV light or ozone, that kills any unwanted bacteria that may have contaminated the plant. A "chemical sterilizing process" is a method of sterilizing which includes exposing the hemp powder to an anti-bacterial chemical agent, such as an organic solvent.

The obvious benefit of whole hemp powder is it contains everything in the plant. By preserving all of the what is in the plant Whole Hemp Powder offers full spectrum causing a symphony effect in the powder maximizing everything.

Whole Hemp Powder (WHP) is safer than highly pure extracts. Isolates can be dangerous if to much is consumed at one time. WHP does not purify a single extract into a highly concentrated form. It includes several components of the plant, each of which is more dilute by virtue of the inclusion of the other components. Thus, it is generally safer, making it much more difficult for an adverse side effect from over-exposure to a single compound. Additionally, WHP is a relatively simple and low cost method of preparing a hemp based product. For example a Kilogram of CBD isolate sells for $7500 to $12,000. One (1) Kilogram of WHP only cost $2500.

The whole green coffee bean powder prepared using the methods described herein may be combined with the whole hemp powder prepared in the manner described above. However, the whole green coffee bean powder may also optionally be combined with a mixture containing hemp derived products. For example, more convention hemp products such as CBD, including CBD oils, may be combined with the whole green coffee bean powder.

Whereas, the present invention has been described in relation to the drawings attached hereto, it should be understood that other and further modifications, apart from those shown or suggested herein, may be made within the spirit and scope of this invention. Descriptions of the embodiments shown in the drawings should not be construed as limiting or defining the ordinary and plain meanings of the terms of the claims unless such is explicitly indicated.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention. CLAIMS

The invention claimed is:

1. A composition comprising:
 a whole hemp powder prepared by a method comprising the steps of:
 a) reducing the moisture content of hemp plants to less than about 5% using a dehumidifier and without exposing the hemp plants to temperatures above 100° Fahrenheit for more than several seconds;
 b) grinding the hemp plants to form a hemp powder capable of passing through a screen of 30 to 100 mesh; and,
 c) sterilizing the hemp powder using a non-chemical process comprising one or more of UV light and ozone; and,
 a whole green coffee bean powder prepared by a method comprising the steps of:
 a) selecting the whole green coffee beans which have been removed from coffee cherries in their fresh green unroasted state with naturally-occurring levels of phytonutrients and having a moisture content;
 b) sterilizing the unroasted whole green coffee beans;

c) reducing the moisture content of the unroasted whole green coffee beans to less than about two percent;

d) grinding the unroasted whole green coffee beans to form a material capable of passing through a 20 mesh screen; and e) mixing at least one stabilizer into the material to obtain a stabilized whole green coffee bean mixture;

wherein all of the aforesaid steps are accomplished without exposing the unroasted whole green coffee beans to temperatures above 130° Fahrenheit for more than several seconds; and wherein the sterilizing the unroasted whole green coffee beans comprises saturating the unroasted whole green coffee beans with an organic solvent.

2. The composition of claim 1 wherein the hemp product is a mixture comprising CBD.

3. The composition of claim 1, wherein the whole green coffee beans comprise *Coffea robusta* coffee beans.

4. The composition of claim 1, wherein the phytonutrients include chlorogenic acid and wherein the unroasted whole green coffee bean is not exposed to temperatures above 100 degrees Fahrenheit.

5. The composition of claim 1, wherein the at least one stabilizer comprises at least one of: Magnesium Silicate; Silicon Dioxide; Tricalcium Phosphate.

6. The composition of claim 1, wherein the stabilized whole green coffee bean mixture includes at least two percent by weight of chlorogenic acid.

7. The composition of claim 1, wherein the at least one stabilizer comprises all of: Magnesium Silicate; Silicon Dioxide; and Tricalcium Phosphate.

8. The composition of claim 1, wherein the step of grinding the unroasted whole green coffee beans comprises a plurality of iteratively finer grinding steps.

9. The composition of claim 8, wherein the step of grinding the unroasted whole green coffee beans comprises at least three iteratively finer grinding steps.

10. The composition of claim 1 wherein the organic solvent comprises 70% isopropyl alcohol.

11. A stabilized composition comprising:

a whole hemp powder prepared by a method comprising the steps of:

a) reducing the moisture content of hemp plants to less than about 5% using a dehumidifier and without exposing the hemp plants to temperatures above 100° Fahrenheit for more than several seconds;

b) grinding the hemp plants to form a hemp powder capable of passing through a screen of 30 to 100 mesh; and, c) sterilizing the hemp powder using a non-chemical process comprising one or more of UV light and Ozone; and, an unroasted whole green coffee bean mixture comprising:

a material derived from whole green coffee beans which have been removed from coffee cherries, in their fresh green unroasted state with naturally-occurring levels of phytonutrients, by sterilizing the unroasted whole green coffee beans and grinding the whole green coffee beans to a size capable of passing a 20 mesh screen; and at least one stabilizer;

wherein the material has not been exposed to temperatures above 100 degrees Fahrenheit for more than several seconds; and, wherein a moisture content of the stabilized unroasted whole green coffee bean mixture is less than about two percent; and wherein the sterilizing the unroasted whole green coffee beans comprises saturating the unroasted whole green coffee beans with an organic solvent.

12. The composition of claim 11 wherein the hemp product is a mixture containing CBD.

* * * * *